United States Patent [19]
Dutcher et al.

[11] Patent Number: 5,255,693
[45] Date of Patent: Oct. 26, 1993

[54] CARDIAC LEAD

[75] Inventors: Robert G. Dutcher; John C. Hill; Robert J. Scott, all of Minneapolis, Minn.

[73] Assignee: Possis Medical, Inc., Minneapolis, Minn.

[21] Appl. No.: 896,663

[22] Filed: Jun. 10, 1992

Related U.S. Application Data

[60] Continuation-in-part of Ser. No. 707,681, May 30, 1991, Pat. No. 5,143,090, which is a continuation-in-part of Ser. No. 600,627, Oct. 22, 1990, Pat. No. 5,040,545, which is a division of Ser. No. 430,596, Nov. 2, 1989, Pat. No. 4,972,847.

[51] Int. Cl.⁵ ............................................. A61N 1/05
[52] U.S. Cl. .................................. 607/120; 128/790; 128/419 P
[58] Field of Search ............... 128/783, 784, 785, 786, 128/790, 419 P

[56] References Cited

U.S. PATENT DOCUMENTS

| | | | |
|---|---|---|---|
| 4,502,492 | 3/1985 | Bornzin | 128/785 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,711,251 | 12/1987 | Stokes | 128/784 |
| 4,750,977 | 6/1988 | Marrese | 204/27 |
| 4,784,161 | 11/1988 | Skalsky et al. | 128/785 |
| 4,819,661 | 4/1989 | Heil, Jr. et al. | 128/786 |
| 4,819,662 | 4/1989 | Heil, Jr. et al. | 128/786 |
| 4,844,099 | 7/1989 | Skalsky et al. | 128/785 |
| 4,953,564 | 9/1990 | Berthelsen | 128/784 |
| 4,972,848 | 11/1990 | Di Domenico et al. | 128/785 |
| 5,002,067 | 3/1991 | Berthelsen et al. | 128/786 |
| 5,003,992 | 4/1991 | Holleman et al. | 128/785 |
| 5,074,313 | 12/1991 | Dahl et al. | 128/419 P |

*Primary Examiner*—Kyle L. Howell
*Assistant Examiner*—George Manuel
*Attorney, Agent, or Firm*—Burd, Bartz & Gutenkauf

[57] ABSTRACT

A cardiac lead for transmitting electric current to the heart and/or sensing and monitoring electrical activity of the heart has an elongated electrical conductor connected to a head. An electrode mounted on the head comprises a helical wire adapted to be turned into heart tissue. The helical wire is coated with platinum black particles which decrease electrical losses at the electrode-tissue interface. A plug impregnated with a drug located within the head is in contact with the helical wire and platinum black particles thereon. The drug migrates from the plug to the active outer end section of the electrode.

18 Claims, 2 Drawing Sheets

CARDIAC LEAD

CROSS REFERENCE TO RELATED APPLICATION

This application is a continuation-in-part of U.S. application Ser. No. 707,681 filed May 30, 1991. Application Ser. No. 707,681 is a continuation-in-part of U.S. application Ser. No. 600,627 filed Oct. 22, 1990, now U.S. Pat. No. 5,040,545. application Ser. No. 600,627 is a division of U.S. application Ser. No. 430,596 filed Nov. 2, 1989, now U.S. Pat. No. 4,972,847.

FIELD OF INVENTION

The invention relates to cardiac leads connectable to a heart for transmitting electric signals to the heart and monitoring the electrical activity of the heart. The cardiac leads also dispense a steroid or other drugs adjacent the stimulation site.

BACKGROUND OF THE INVENTION

A myocardial lead having a rigid helical coil adapted to be turned into heart tissue is disclosed by L. R. Bolduc in U.S. Pat. No. 3,737,579. The helical coil is a wire connected with an elongated flexible conductor to a pacemaker for transmitting electrical pacing currents to the heart. Interactions between the coil and the heart tissue can reduce the effects of the electrical stimulation. Fibrosis can occur around the coil which increases the chronic threshold and can result in trauma of the heart tissue to be stimulated. The configuration of the electrode can reduce mechanical trauma and minimize fibrosis. Fibrotic formation can also be reduced by the administration of suitable drugs to the stimulation site. The delivery of a steroid drug to the stimulation site of an implantable pacing lead is disclosed by W. A. Berthelsen in U.S. Pat. No. 4,953,564. A controlled drug release device is integrated with the fixation helix such that as the helix is extended the controlled drug release device is concurrently extended. The controlled drug release device is limited to the immediate vicinity of the distal end of the helix to minimize the dispersion of the drug into the blood stream. The controlled drug release device has a porous elution path for accommodating the dispensing steroid.

SUMMARY OF THE INVENTION

The invention relates to a cardiac lead connectable to an implantable cardiac arrhythmia management device (not shown) for transmitting electric current to the heart and/or sensing and monitoring the electrical activity of the heart. The implantable cardiac arrhythmia management device includes but is not limited to cardiac pacemakers and automatic implantable cardiac defibrillators (AICD). The lead has an elongated flexible conductor enclosed within a sheath of nonelectrically conductive material to electrically connect the cardiac management device with an electrode adapted to be implanted in or on heart tissue. The electrode is supported on a head of non-electrically conductive material and joined to the conductor. In one form of the invention the electrode is a helical wire having a portion located externally of the head adapted to be turned into the heart tissue to secure the lead to the heart tissue and transmit electrical signals thereto or receive electrical signals therefrom. The helical wire has an inner end extended into the head to support the wire on the head. The wire has at least one helical coil projected away from the generally flat face of the head. A sheath of non-electrically conductive material surrounds the outer end of the wire adjacent the head except for a distal portion thereof which represents the electrode. The external portion of the electrode has an outer surface covered with a layer of platinum black particles. The remainder of the wire can have a porous outer coating which is a continuation of the platinum black particles. Other types of coatings can be applied to the wire to carry a drug from a source of the drug in the head to the electrode. The sheath covers the coating on the wire except for the distal portion thereof. The layer of platinum black particles has generally uniform particle size and generally uniform particle distribution on the outer surface of the wire. The platinum black particles on the distal portion of the electrode has a generally uniform microporous outer surface in contact with the heart tissue which decreases electrical losses at the electrode tissue interface, increases the current density to the heart tissue, establishes intimate contact between the electrode and myocardium tissue, lowers stimulation thresholds, and increases amplitude of electrical signals from the myocardium.

A plug of material that accommodates a drug, such as a steroid, is mounted in the head within the confines of the base of the helical wire. The plug is a cylindrical member coaxially aligned with the longitudinal axis of the helical electrode. The base has a generally cylindrical recess or pocket surrounded by the inner end section of the helical wire. A portion of the wire and any coating thereon is exposed to the pocket. A plug of material, such as silicone rubber, porous glass, ceramic, plastic or metal, or elastic absorbant material, such as cellulose or natural sponge is located in the pocket in the head. The coating on the inner end section can be in contact with the plug. The drug in the plug migrates along the porous material on the helical wire toward the distal end of the wire which is the electrode. The drug is dispensed at the stimulation site to augment the function of stimulation as well as reduce irritability, fibrous formation and arrhythmias. The steroid is incorporated into the material and in use elute out of the material in the presence of body fluid. The drug can be incorporated into a plastic material during the polymerization process. Other types of coatings including but not limited to pyrolytic carbon, titanium nitride, and other surfaces can be used to enhance the electro-tissue interface between the electrode and heart tissue and carry the drug from the plug to the distal end of the helical wire for dispensing at the stimulation site.

DESCRIPTION OF PREFERRED EMBODIMENT OF THE INVENTION

Figure 1:
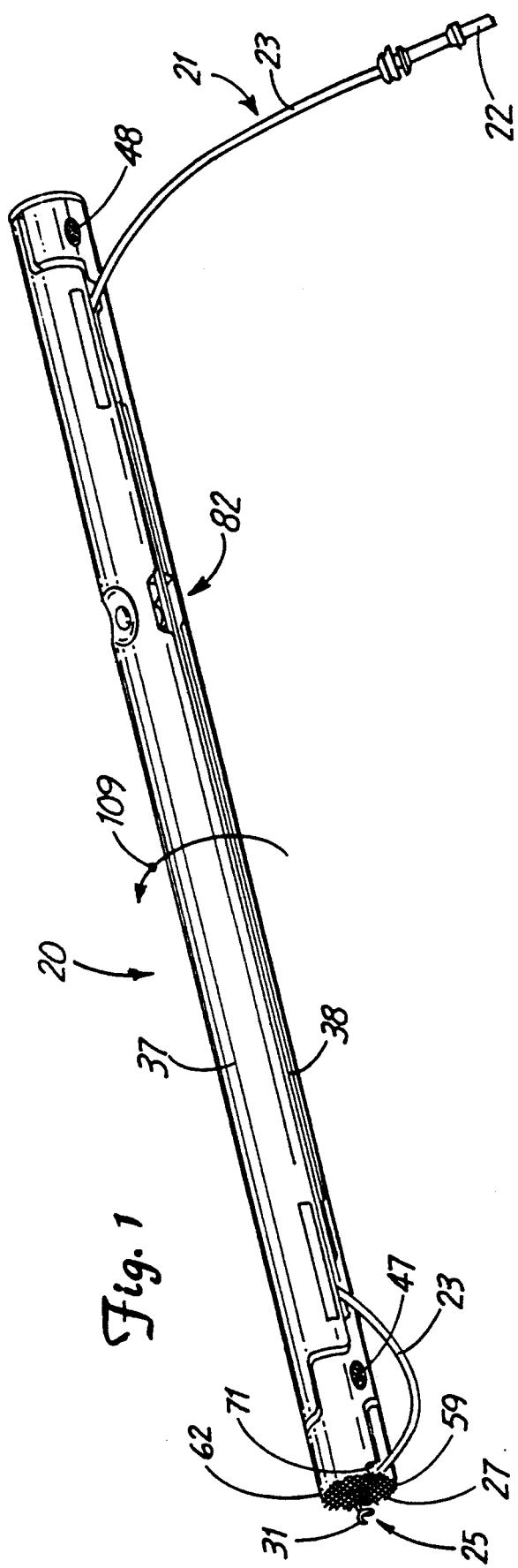
FIG. 1 is a perspective view of a cardiac lead insertion tool holding an implantable cardiac lead having a myocardial helical electrode.
Figure 2:
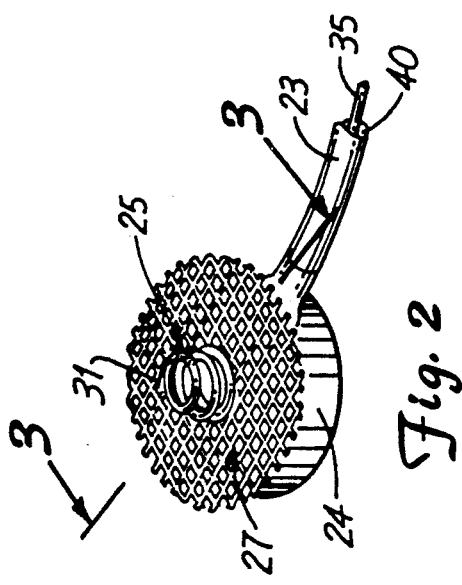
FIG. 2 is a perspective view of the distal end of the cardiac lead shown in FIG. 1.
Figure 3:
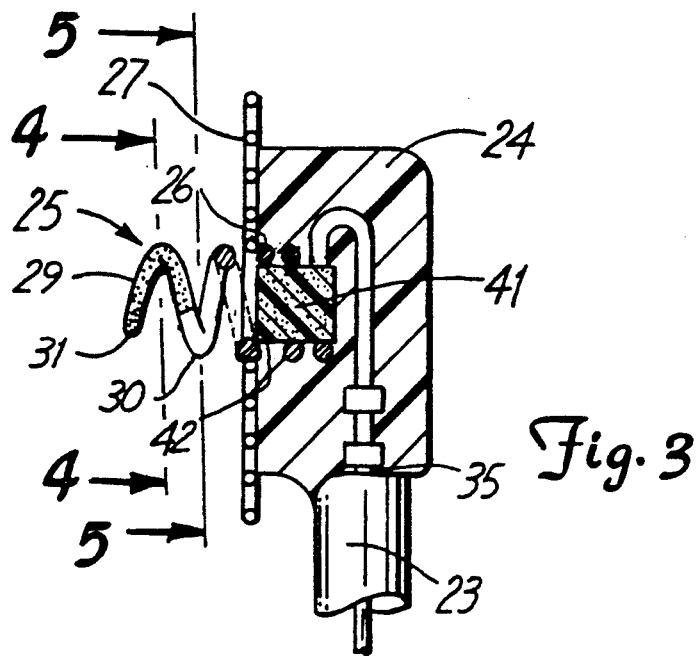
FIG. 3 is an enlarged sectional view taken along line 3—3 of FIG. 3.

Referring to FIG. 1, there is shown the myocardial lead installation tool known as an introducer, indicated generally at 20, holding a cardiac lead, indicated generally at 21, prior to the implantation of the electrode of the lead into the myocardium of a heart. Introducer 20 is disclosed in U.S. Pat. No. 4,972,847, incorporated herein by reference. Lead 21 has a connector 22 at the proximal end thereof adapted to be connected to terminal of a cardiac management device (not shown) operable to generate heart pacing currents. Connector 22 is joined to an elongated flexible electrical conductor 23 having a distal end joined to a generally cylindrical head 24. Head 24 is made of non-electrical conductive material that is biocompatible, such as medical grade silicone rubber. A rigid helical electrode, indicated generally at 25, having several convolutions is mounted on the center of head 24. Electrode 25 projects outwardly from the central portion of head 24 to enable the outer section thereof to be turned into the myocardium. As shown in FIG. 3, electrode 25 has an inner end section 26 embedded in head 24 and connected to conductor wire 35 of conductor 23. Wire 35 is a multifilar electrical conductor coil made of nickel cobalt wire or other suitable conducting material. Wire 35 is enclosed within non-electrical conductive sheath 40 that is biocompatible, such as medical grade silicone rubber. A generally flat circular netting 27 surrounds electrode 25. Netting 27 is joined to the distal face of head 24 by bonding it directly to the silicone rubber of head 24. Other suitable connecting materials can be used to attach netting 27 to head 24. The outer peripherial edge of netting 27 projects radially outward from head 24 to increase the surface engagement with the heart tissue. Netting 27 can be a porous polyester fiber that enhances fibroic growth to insure a secure connection of electrode 25 to the heart tissue.

Figure 4:
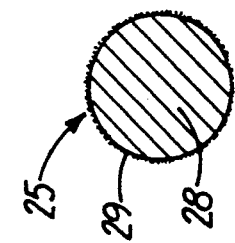
FIG. 4 is an enlarged sectional view taken along line 4—4 of FIG. 3.
Figure 5:
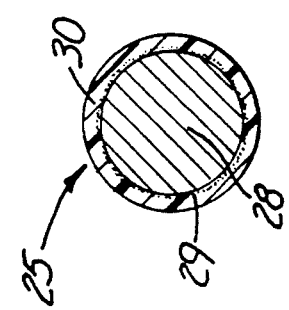
FIG. 5 is an enlarged sectional view taken along line 5—5 of FIG. 3.
Figure 6:
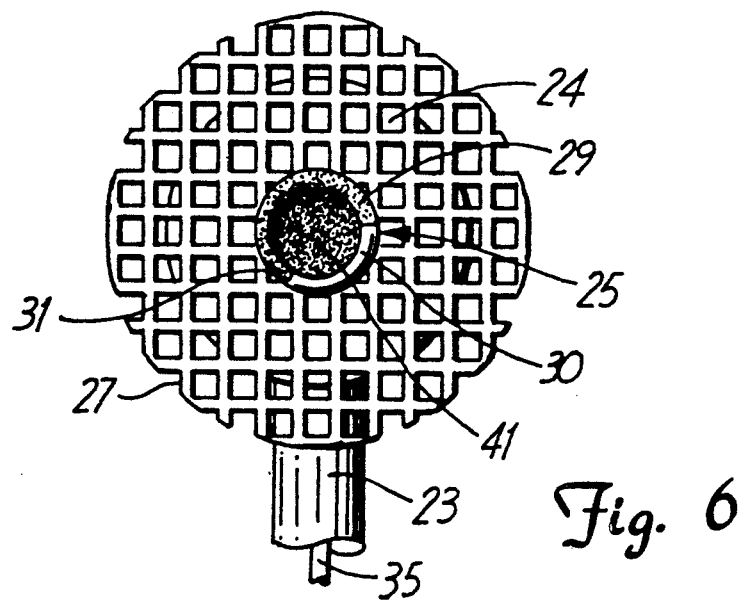
FIG. 6 is an enlarged top plan view of the cardiac lead shown in FIG. 2.

Helical electrode 25 is a rigid helical wire 28 terminating in a pointed or sharpened end 31. A sheath 30 of non-electrical conductive material, such as medical grade silicone rubber, covers wire 28 except for about the end one half turn portion thereof, such as between 160 and 190 degrees of the end portion of wire 28. This end portion of wire 28 comprises the active electrode. Wire 28 can be made of a platinum/iridium. The entire exterior surface of the end one half turn section of wire 28 is completely covered with a coat or layer of platinum black particles 29 to substantially reduce electrode polarization and facilitate the dispensing of a drug to the stimulation site. Wire 28 is platinized to develop the coating of platinum black particles 29. The entire wire 28 is coated with a continuous layer of platinum black particles 29 as shown in FIGS. 3, 4 and 5. The platinum black particles 29 have a micro-porous surface of submicron size particles. The layer of platinum black particles 29 is electrochemically plated onto the outer surface of the wire 28. The wire 28 is placed in a platinum ion plating solution and subjected to an electric d.c. current. The plating solution and wire 28 are also subjected to intermittent ultrasonic vibrations that agitate the platinum ions. The electric current is terminated during the vibration period. The time period between vibration episodes can be varied. An oscillating piezoelectric ceramic is used to generate vibrations at a selected frequency that produces uniform particle size and particle distribution. The submicron size particles of platinum black particles 29 are bonded to the entire outside surface of wire 28 up to and into head 24 as seen in FIGS. 3 and 4. The platinum black particles 29 have generally uniform particle size and particle distribution resulting in generally uniform current density over the layer of platinum black particles 29 and lower stimulation thresholds. The current carried by lead 21 is delivered to the heart muscle almost exclusively through the platinum black particles 29 at the outer end of wire 28 as the remainder of wire is covered with sheath 30 and head 24. As shown in FIGS. 3, 4 and 6, layer of platinum black particles 29 has a continuous microporous surface which provides for intimate contact between the end portion of electrode 25 and the myocardial tissue and an increase in real surface area with a resulting decrease in electrode-tissue interface electrical losses and maximized voltage applied to the stimulatable tissue of the heart and thereby lower stimulation thresholds and increase intracardiac electrical signal sensing. The layer of platinum black particles 29 on the entire wire 28 aids in the movement of a drug from a drug source in head 24 to the stimulation site. Other types of materials can be located on wire 28 to enhance the electrical tissue interface between the active electrode and the heart tissue and facilitate the dispensing of a drug to the stimulation site.

As shown in FIG. 3, the mid-section of the inner side of head 24 has a cylindrical recess or pocket 42 accommodating a plug 41 impregnated with a drug for elution at the stimulation site. Plug 41 is secured to head 24 with suitable bonding material. The inner end section 26 of the wire 28 is turned around the outer circumference of plug 41 to locate the plug 41 in co-axial alignment with the helical electrode 25. The porous coating on the inner end section 29 may be in contact with the outer surface of plug 41 to allow the drug to migrate from plug 41 along the wire to the outer end thereof for dispensing at the stimulation site. The drug will also be dispensed from the outer end of plug 41 to the heart tissue.

Plug 41 is a solid cylindrical one piece plastic material, such as polyurethane, impregnated with the drug having an axis coaxially aligned with the longitudinal axis of helical electrode 25. Other types of materials including but not limited to silicone rubber, porous glass, porous ceramic, porous metal and like bio-compatable materials can be used for plug 41 to accommodate the drug.

Examples of the drug incorporated into the material of plug 41 include steroids, such as glucocorticosteroids, and sodium salt of dexamethasone phosphate. Other drugs that can be incorporated into plug 41 are disclosed by Di Domenico et al in U.S. Pat. No. 4,972,848, incorporated herein by reference.

Returning to FIG. 1, introducer 20 has a pair of elongated beams 37 and 38 pivotly connected at their opposite ends with pivot members 47 and 48. The distal ends of beams 37 and 38 have a pair of arcuate jaws 59 and 62 for gripping opposite sides of head 24 of lead 21. Beams 37 and 38 have a slot 71 adjacent jaws 59 and 62 which allows conductor 23 to b located between beams 37 and 38. A releasable lock mechanism indicated generally at 82 holds the beams 37 and 38 to a closed position to maintain the gripping force of jaws 59 and 62 on head 24. Releasable lock mechanism 82 can be disengaged to allow beams 37 and 38 to move to an open position releasing the grip of jaws 59 and 62 on head 24. Introducer 20 is rotated in the direction of the arrow 109 during the implant procedure of helical electrode 25. Only a small keyhole opening in the chest wall is required to implant the lead. The detailed structure and operation of introducer 20 is disclosed in U.S. Pat. No. 4,972,847, incorporated herein by reference.

The dispensing of a steroid drug at the stimulation site is enhanced by the drug migrating to the porous coating of platinum black particles at the outer end of the electrode 25. The drug augments the function of stimulation and reduces the pacing and sensing thresholds. The drug also reduces irritability and fibris formation and minimizes other electrode related problems including inflammation and arrhythmias. The current carried by lead 21 is delivered to the heart muscle almost exclusively through platinum black particles 29 and the micro-porous surface of the platinum black particles is in intimate contact with the myocardial tissue. The presence of the steroid drug in the micro-porous surface lowers stimulation thresholds and increases cardiac electrical signal sensing.

While there have been shown and described preferred embodiment of the cardiac lead of the invention. It is understood that changes in the structure, arrangement of structure and materials may be made by those skilled in the art without departing from the invention. The invention is defined in the following claims.

We claim:

1. A cardiac lead connectable to a cardiac management device for transmitting electric current to and/or receiving electrical signals from the myocardium of the heart comprising: an elongated flexible conductor wire means, sheath means of non-electrical conductive material surrounding said conductor wire means, an electrical connector attached to the wire means adapted to be connected to a cardiac management device, a head of non-electrically conductive material connected to said conductor wire means and sheath means, a helical electrode having a first end section extended into said head and connected to said conductor wire means and a helical second end section extended from said head adapted to be screwed into the myocardium of a heart, said second end section having an outer helical surface terminating in a point, a layer of platinum black particles attached to substantially the entire outer helical surface of the second end section, said layer of platinum black particles having generally uniform particle size and generally uniform distribution on said outer surface of the second end section of the electrode whereby said layer has a continuous and generally uniform microporous outer platinum black surface locatable in surface contact with the myocardium of the heart whereby said layer of platinum black particles decreases electrical losses at the electrode-tissue interface, establishes intimate contact between the electrode and myocardium, and maximizes voltage applied to said myocardium and lowers stimulation thresholds and increases amplitude of sensed electrical signals from the myocardium.

2. The lead of claim 1 including: porous means secured to the head surrounding said helical second end section to enhance fibrotic growth to connect the head and second end section to the myocardium.

3. The lead of claim 2 wherein: the porous means is a generally circular shaped fabric secured to the head.

4. The lead of claim 1 wherein: said layer of platinum black particles are electrochemically plated on the entire outer surface of the exposed external second section of the electrode.

5. The lead of claim 1 including: sheath means of non-electrically conductive material extended from said head covering a portion of the helical second section of said electrode, said second section having an end portion projected from said sheath means, said end portion having an outer surface covered with said platinum black particles.

6. The lead of claim 1 including: sheath means of non-electrical conductive material joined to the head covering a portion of the helical second section of said electrode, said helical electrode having about one half turn end portion extended from said sheath, said end portion having an outer surface covered with said platinum black particles.

7. A cardiac lead connectable to a cardiac management device for transmitting electric current to and/or receiving electrical signals from the myocardium of the heart comprising: an elongated flexible conductor wire means, sheath means of non-electrical conductive material surrounding said conductor wire means, an electrical connector attached to the wire means adapted to be connected to a cardiac management device, a head of non-electrically conductive material connected to said conductor wire means and sheath means, a helical electrode having a first end section extended into said head and connected to said conductor wire means and a helical second end section extended from said head adapted to be screwed into the myocardium of a heart, said second end section terminating in a point, said helical electrode having an outer surface, a layer of platinum black particles attached to substantially the entire outer surface of the helical electrode, said layer of platinum black particles having substantially uniform particle size and uniform distribution on said outer surface of the electrode whereby said layer has a generally has continuous and uniform microporous outer platinum black surface locatable in surface contact with the myocardium of the heart whereby said layer of platinum black particles decreases electrical losses at the electrode-tissue interface, establishes intimate contact between the electrode and myocardium, and maximizes voltage applied to said myocardium and lowers stimulation thresholds and increases amplitude of sensed electrical signals from the myocardium and a plug impregnated with a drug mounted on the head, said first end section of the helical electrode and platinum black particles thereon being engageable with the plug to permit the drug to move from the plug to the second end section of the helical electrode.

8. The lead of claim 7 including: porous means secured to the head surrounding said helical second end section to enhance fibrotic growth to connect the head and second end section to the myocardium.

9. The lead of claim 8 wherein: the porous means is a generally circular shaped fabric secured to the head.

10. The lead of claim 7 including: sheath means of non-electrically conductive material extended from said head covering a portion of the helical second section of said electrode and platinum black particles thereon, said second section having an end portion projected from said sheath means, said end portion having an outer surface covered with said platinum black particles.

11. The lead of claim 7 including: sheath means of non-electrical conductive material joined to the head covering a portion of the helical second section of said electrode and platinum black particles thereon, said helical electrode having about one half turn end portion extended from said sheath, said end portion having an outer surface covered with said platinum black particles.

12. The lead of claim 7 wherein: said head has a pocket, said plug being located within said pocket, said first end section of the helical electrode surrounding said plug with the platinum black particles thereon in engagement with the plug.

13. The lead of claim 12 wherein: the pocket has a cylindrical shape, said plug having a cylindrical shape and size to fill the pocket and an axis aligned with the longitudinal axis of the helical electrode.

14. A cardiac lead connectable to a cardiac management device for transmitting electric current to and/or receiving electrical signals from the heart comprising: an elongated flexible conductor wire means, sheath means of non-electrical conductive material surrounding said conductor wire means, an electrical connector attached to the wire means adapted to be connected to a cardiac management device, a head of non-electrically conductive material connected to said conductor wire means and sheath means, an electrode having a first end section extended into said head and connected to said conductor wire means and a second helical end section extended from said head adapted to engage heart tissue, sheath means of non-electrical conductive material extended from the head covering a portion of the helical second section of said electrode, said helical electrode having about one-half turn end portion extended from said sheath, means accommodating a drug mounted on the head, said electrode having an outer surface, means attached to the outer surface of the electrode engageable with the means accommodating a drug and the heart tissue at the second end section thereof for decreasing electrical losses at the electrode-tissue interface, maximizing voltage applied to said heart tissue, lower stimulation thresholds and increase amplitude of sensed electrical signals from the heart tissue and dispense the drug adjacent the stimulation site, said end portion having an outer surface covered with said means for decreasing electrical losses at the electrode tissue interface and dispense the drug adjacent the stimulate site.

15. The lead of claim 14 including: porous means secured to the head surrounding said second end section to enhance fibrotic growth to connect the head and second end section to the heart tissue.

16. The lead of claim 14 wherein: said head has a pocket, said plug being located within said pocket, said first end section of the electrode being engageable with said plug whereby drug from the plug migrates to the second end section of the electrode and dispenses to the stimulation site.

17. The lead of claim 16 wherein: the pocket has a cylindrical shape, said plug having a cylindrical shape and size to fill the pocket.

18. The lead of claim 14 wherein: said means attached to the outer surface of the electrode comprises platinum black particles.

* * * * *